United States Patent [19]

Bühmann et al.

[11] Patent Number: 5,066,675
[45] Date of Patent: Nov. 19, 1991

[54] SUBSTITUTED PHENYL ACID ESTERS, THEIR PREPARATION AND THEIR USE AS INSECTICIDES AND ACARICIDES

[75] Inventors: Ulrich Bühmann; Hartmut Joppien; Dietrich Baumert, all of Berlin, Fed. Rep. of Germany

[73] Assignee: Schering Aktiengesellschaft, Fed. Rep. of Germany

[21] Appl. No.: 575,674

[22] Filed: Aug. 31, 1990

Related U.S. Application Data

[63] Continuation-in-part of Ser. No. 403,023, Aug. 31, 1989, abandoned, which is a continuation of Ser. No. 85,973, Aug. 14, 1987, abandoned.

[30] Foreign Application Priority Data

Aug. 15, 1986 [DE] Fed. Rep. of Germany ....... 3627712

[51] Int. Cl.$^5$ ............................................. A01N 37/10
[52] U.S. Cl. .................................... 514/544; 514/517; 514/522; 514/531; 514/538; 558/29; 558/32; 558/414; 560/9; 560/11; 560/19; 560/20; 560/55; 560/75; 560/102; 560/105
[58] Field of Search ...................... 560/105, 9, 11, 19, 560/20, 55, 75, 102; 558/29, 32, 414; 514/544, 517, 522, 531, 538

[56] References Cited

U.S. PATENT DOCUMENTS

| | | | |
|---|---|---|---|
| 4,016,179 | 4/1977 | Fujimoto | 560/55 |
| 4,091,111 | 5/1978 | Ohno | 560/105 |
| 4,668,815 | 5/1987 | Enari | 560/55 |

OTHER PUBLICATIONS

Elliott, Synthetic Pyrethroids, ACS, Symposium Series No. 42, pp. 1-28 (1977).

*Primary Examiner*—Michael L. Shippen
*Attorney, Agent, or Firm*—Ostrolenk, Faber, Gerb & Soffen

[57] ABSTRACT

There are described new phenylacetic acid derivatives of general formula I

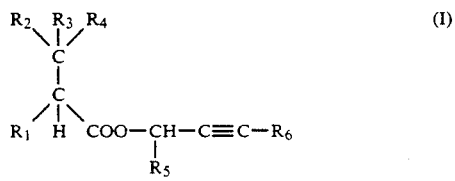

in which
$R_1$, $R_2$, $R_3$, $R_4$, $R_5$ and $R_6$ have the meanings given in the description, processes for their preparation and insecticidal and acaricidal compositions containing these compounds.

11 Claims, No Drawings

SUBSTITUTED PHENYL ACID ESTERS, THEIR PREPARATION AND THEIR USE AS INSECTICIDES AND ACARICIDES

This application is a continuation in part of application Ser. No. 403023, filed Aug. 31, 1989, now abandoned, which itself is a continuation of our application Ser. No. 85973, filed 14 Aug. 1987, now abandoned.

This invention relates to new substituted phenylacetic acid esters, processes for their preparation and their use as pesticides with insecticidal and acaricidal activity.

In UK Patent No 2161163 (equivalent to U.S. Pat. No. 4,668,815—Enari et al), there are disclosed compounds of the following formula, having insecticidal activity,

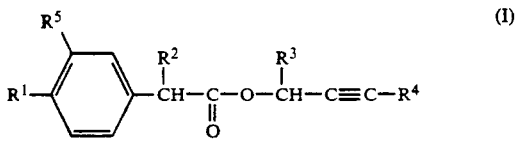

wherein $R^1$ is halogen or alkyl; $R^5$ is hydrogen or halogen; $R^3$ is hydrogen or methyl; $R^4$ is hydrogen, lower alkyl, various alkenyl, alkynyl and substituted methyl groups, as well as acetyl and methoxycarbonyl; and $R^2$ is lower alkyl. In this patent, the only compounds disclosed are those where $R^2$ is isopropyl. We have now found that compounds of a similar structure, where $R^2$ is a tertiary alkyl group, have particularly advantageous properties. In particular where we have compared them with the prior art analogues, where $R^2$ is isopropyl, we have shown that the compounds of the present invention have improved activity against certain pests.

We have also found that the compounds of the invention have greater stability, e.g. in soil, than the isopropyl analogues in UK Patent 2161163, with which they have been compared. This is particularly advantageous in combating soil based pests, such as Diabrotica spp.

Thus according to the invention there are provided phenylacetic acid derivatives of general formula I

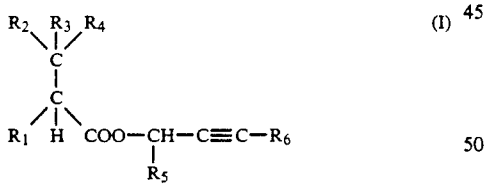

in which $R_1$ is phenyl, optionally substituted by one or more of the same or different groups selected from halogen, hydroxy, $C_{1-4}$-alkyl, halo-$C_{1-4}$-alkyl, $C_{3-6}$-cycloalkyl, halo-$C_{3-6}$-cycloalkyl, $C_{1-6}$-alkoxy, (optionally substituted by halogen, $C_{1-4}$-alkoxy, $C_{1-4}$-alkylthio, $C_{1-4}$-alkylamino or di-$C_{1-4}$-alkylamino , $C_{2-6}$-alkynyloxy, halo-$C_{2-6}$-alkynyloxy, $C_{2-6}$-alkenyloxy, halo-$C_{2-6}$-alkenyloxy, $C_{3-6}$-cycloalkoxy, (optionally substituted by halogen), $C_{3-6}$-cycloalkylmethoxy, halo-$C_{3-6}$-cycloalkylmethoxy, $C_{1-6}$-alkylthio, (optionally substituted by halogen), $C_{1-6}$-alkylsulphinyl, $C_{1-6}$-alkylsulphonyl, phenoxy, halophenoxy, amino, $C_{1-4}$-alkylamino, di-$C_{1-4}$-alkylamino, cyano, nitro and the group OX, wherein X is the acyl group $R_7CO$ or the sulphonyl group $R_7SO_2$, in which $R_7$ is $C_{1-6}$-alkyl, (optionally substituted by halogen, $C_{1-4}$-alkoxy, $C_{1-4}$-alkylamino or di-$C_{1-4}$-alkylamino), $C_{3-6}$-cycloalkyl, (optionally substituted by halogen), $C_{2-6}$-alkynyl, (optionally substituted by halogen), $C_{2-6}$-alkenyl or phenyl;

$R_2$, $R_3$ and $R_4$ are the same or different and are $C_{1-4}$-alkyl, optionally substituted by halogen, $C_{1-4}$-alkoxy and/or $C_{1-4}$-alkylthio;

$R_5$ and $R_6$ are the same or different and are hydrogen, $C_{1-4}$-alkyl or $C_{3-6}$-cycloalkyl, each optionally substituted by halogen, $C_{1-4}$-alkoxy, $C_{1-4}$-alkylthio, $C_{1-4}$-alkylamino or di-$C_{1-4}$-alkylamino; $C_{2-6}$-alkenyl or $C_{2-6}$-alkynyl, each optionally substituted by halogen, or $C_{1-6}$-alkyl, substituted by the group —OY, wherein Y is hydrogen, the acyl group $R_7CO$ or the sulphonyl group $R_7SO_2$, in which $R_7$ has the meaning given above.

The designation "halo" in compounds with the groups alkyl, cycloalkyl, alkoxy, alkylthio, alkenyl, alkynyl, alkenyloxy, alkynyloxy, cycloalkoxy, cycloalkylmethoxy, phenyl or phenoxy means that one or more hydrogen atoms are replaced by halogen. By the term halogen is to be understood fluorine, chlorine, bromine and iodine.

A particularly preferred group of compounds are those where:

$R_1$ is phenyl, substituted in the para position by $C_{1-3}$-methyl, halogen (especially chlorine), trifluoromethyl, $C_{1-2}$-alkoxy or $C_{1-2}$-fluoroalkoxy, and optionally substituted in the meta position by fluorine or chlorine;

$R_2$, $R_3$ and $R_4$ are methyl;

$R_5$ is hydrogen or acetylenyl; and $R_6$ is hydrogen or methyl.

The invention includes individual isomers as well as mixtures of these.

The compounds of the invention can be prepared according to known processes. One process comprises the treatment of a compound of formula II

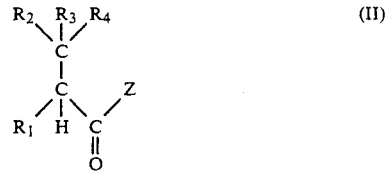

in which $R_1$, $R_2$, $R_3$ and $R_4$ have the meanings given above and Z is halogen or hydroxy, with an alcohol of general formula III

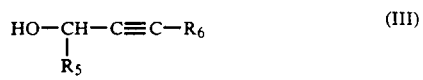

in which $R_5$ and $R_6$ have the meanings given above.

In the case of the reaction of compounds of general formula II in which Z=halogen, an alcohol of formula III is acylated with a carboxylic acid halide (cf. e.g. "Reaktionen und Synthesen im organish chemischen Praktikum, L.F. Tietze—Th. Eicher, Thieme Verlag Stuttgart, 1981, page 115). The reaction is suitably carried out in the presence of an acid acceptor (cf. "Houben-Weyl, Methoden der organischen Chemie", Band VIII, p. 541 ff, Georg Thieme Verlag, Stuttgart 1952).

Conventional basic materials are suitable as acid acceptors, such as for example aliphatic, aromatic and heterocyclic amines, e.g. triethylamine, dimethylamine, piperidine and pyridine. The reaction can be carried out with or without a solvent. In addition to the acid acceptors, suitable solvents or their mixtures include optionally chorinated aliphatic and aromatic hydrocarbons, such as petroleum ether, benzene, toluene, xylene, dichloromethane, chloroform, carbon tetrachloride, 1,2-dichloroethane and chlorobenzene; ethers, such as diethyl and di-n-butyl ether, methyl tert-butyl ether, tetrahydrofuran and dioxane; ketones, such as acetone, methyl ethyl ketone and methyl isopropyl ketone, and nitriles, such as acetonitrile and propionitrile.

Generally the reaction materials are used in stoichiometric amounts. An excess of one or more can be used in some cases but generally without advantage.

The reaction usually proceeds above 0° C. with adequate speed. Since heat is usually evolved, it is generally advantageous to provide cooling.

When reacting compounds of general formula II, in which Z=hydroxy, with alcohols of formula III, this is an esterification of a carboxylic acid (cf. Houben-Weyl, Methoden der organischen Chemie, Band VIII, p. 516 ff, Georg Thieme Verlag, Stuttgart 1952), which can be speeded up in a known way, optionally by addition of catalysts, such as sulphuric acid, hydrogen halides or sulphonic acids or acid ion exchange resins, and the esterification equilibrium can be pushed into the desired direction by removal, from the reaction mixture, the water or the ester of general formula I, such as for example by azeotropic distillation.

The compounds of the invention of general formula I can also be synthesised according to almost all practical conventional methods for the preparation of esters, such as for example using carboxylic acid anhydrides that can be derived from carboxylic acids of general formula II, or also by reaction of salts of these carboxylic acids with optionally substituted halides of general formula IV

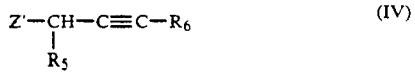

in which $R_5$ and $R_6$ have the meanings given above and $Z'$ is halogen.

The phenylacetic acids used as starting materials of general formula II, in which Z=OH

in which $R_1$, $R_2$, $R_3$ and $R_4$ have the meanings given above, are usually known. They can be prepared according to known processes (see for example J. Org. Chem. 32(9)1967, 2799 and 2801; Chem. Ber. 116(1938), 3708-3724).

The phenylacetyl halides of general formula II in which Z=halogen can be obtained from these free acids in known manner.

The alcohols of general formula III are generally commercial products or can be prepared according to generally known methods.

The compounds of the invention are, as a rule, colourless oils that are highly soluble in practically all organic solvents but are almost insoluble in water.

The compounds of the invention have insecticidal and acaricidal activity and as a result can be used for combating a wide range of insects and acarids, including animal ectoparasites. Examples include Lepidoptera, such as *Plutella xylostella, Spodoptera littoralis, Heliothis armigera* and *Pieris brassicae*; Diptera, such as *Musca domestica, Ceratitis capitata, Erioischia brassicae, Lucilia sericata* and *Aedes aeqypti*; Homoptera, including aphids such as *Megoura viciae* and *Nilaparvata lugens*; Coleoptera, such as *Phaedon cochleariae, Anthonomus grandis* and corn rootworms (*Diabrotica* spp. eg. *Diabrotica undecimpunctata*); Orthoptera, such as *Blattella germanica*; ticks, such as *Boophilus microplus* and lice, such as *Damalinia bovis* and *Linognathus vituli*, as well as spider mites such as *Tetranychus urticae* and *Panonychus ulmi*.

The compounds of the invention are suitable in a surprising manner for combating insects, especially combating pest insects and represent a valuable improvement in the state of the art.

The compounds according to the invention can be used at a concentration of 0.0005 to 5%, preferably from 0.001 to 1%, calculated as gram active material per 100 ml of the composition.

The compounds of the invention can be used either alone or in mixture with each other or another insecticide. Optionally other plant protection or pesticidal compositions, such as for example insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose.

Suitable mixture partners may also include phospholipids, e.g. such as from the group phosphatidylcholine, hydrated phosphatidylcholine, phosphatidylethanolamine, N-acyl-phosphatidylethanolamine, phosphatidylinositol, phosphatidylserine, lysolecithin or phosphatidylglycerol.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons such as benzene, toluene, xylene, cyclohexanone, isophorone, dimethyl sulphoxide, dimethylformamide, other mineral-oil fractions and plant oils.

Suitable solid carriers include mineral earths, e.g. tonsil, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

Formulations can be prepared, for example, from the following ingredients.

A WETTABLE POWDER 20 percent by weight active ingredient
35 percent by weight bentonite
8 percent by weight calcium lignosulphonate
2 percent by weight of the sodium salt of N-methyl-N-oleyltaurine 35 percent by weight silicic acid

B PASTE 45 percent by weight active ingredient
5 percent by weight sodium aluminium silicate
15 percent by weight cetylpolyglycol ether with 8 moles ethylene oxide
2 percent by weight spindle oil
10 percent by weight polyethylene glycol
23 parts water

C EMULSIFIABLE CONCENTRATE 20 percent by weight active ingredient
75 percent by weight isophorone
5 percent by weight of an emulsifier mixture of calcium phenylsulphonate and fatty alcohol polyglycol ether The following examples illustrate the preparation of compounds according to the invention.

EXAMPLE 1

2-Butynyl 2-(4-chlorophenyl)-3,3-dimethylbutyrate

To a solution of 2.43 ml 0.0325 mol) but-2-yn-1-ol and 3.97 g (0.0325 mol of 4-dimethylaminopyridine in 35 ml tetrahydrofuran is added dropwise, at 0°–5° C., a solution of 7.95 g 0.0325 mol 2-(4-chlorophenyl-3,3-dimethylbutyryl chloride in 25 ml tetrahydrofuran. The reaction mixture was allowed to warm to room temperature and after one and a half hours worked up as follows: after removal of the tetrahydrofuran in vacuo, it was treated with water and stirred with ether, the ether phase was dried over magnesium sulphate and concentrated in vacuo. A colourless oil was obtained.

$n_D^{20}$: 1.5221.

Yield: 7.9g = 87% of theory.

Elementary analysis

Calc.: 68.93% C 6.87% H 12.72% Cl.

Found: 68.62% C 6.32% H 13.38% Cl.

Preparation of the Starting Material 2-(4-Chlorophenyl)-3,3-dimethylbutyryl chloride 2.26g (0.01 mol) 2-(4-Chlorophenyl)-3,3-dimethylbutyric acid was treated with 3.7 ml (0.05 mol) thionyl chloride and heated under reflux for 6 hours. The reaction mixture was concentrated in vacuo and the residue taken up in hexane and the solution treated with activated charcoal. After filtration the pure acid chloride was obtained by concentration from the hexane solution.

Yield: 5.43g = 88.9% of theory.

EXAMPLE 2

Propargyl 2-(4-chlorophenyl)-3,3-dimethylbutyrate

To a solution of 5.56 g (0.025 mol) 2-(4-methoxyphenyl)-3,3-dimethylbutyric acid in 50 ml dimethylformamide, was added 5.43 g (0.04 mol) anhydrous potassium carbonate and 1 g of potassium iodide. The mixture was heated to 50° C. and 3.57 g (0.03 mol) bromopropyne was added dropwise. After stirring at 50° C. for two hours the reaction mixture was added to a large amount of water. It was extracted several times with dichloromethane and thoroughly washed with water. The organic phase was dried over magnesium sulphate, filtered and concentrated in vacuo. A colourless oil was obtained which was chomatographed on silica gel .

Yield: 4.62 g = 71% of theory (colourless oil).

$n_D^{20}$:1.5135.

Elementary analysis:

Calc.: 73.82% C 7.74% H.

Found: 74.30% C 7.48% H.

In a similar way the following compounds of formula I were prepared

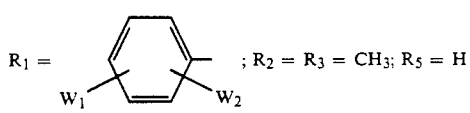

$R_1 = $ ; $R_2 = R_3 = CH_3$; $R_5 = H$

| Example | $W_1$ | $W_2$ | $R_4$ | $R_6$ | $n_D^{20}$/m.p. |
|---|---|---|---|---|---|
| 3 | H | H | $CH_3$ | H | 1.5068 |
| 4 | 4-$CH_3$ | H | $CH_3$ | H | 1.5070 |
| 5 | 4-C($CH_3$)$_3$ | H | $CH_3$ | H | 1.5050 |
| 6 | 4-F | H | $CH_3$ | H | 1.4948 |
| 7 | 4-Br | H | $CH_3$ | H | 1.5328 |
| 8 | 3-Cl | 4-Cl | $CH_3$ | H | 1.5325 |
| 9 | 4-Cl | H | $C_2H_5$ | $CH_3$ | 1.5234 |
| 10 | 4-Cl | H | $C_2H_5$ | H | 1.5229 |
| 11 | 4-Cl | H | $CH_3$ | H | 1.5182 |
| 12 | 4-$OCH_3$ | H | $CH_3$ | $CH_3$ | 1.5166 |
| 13 | 4-OH | H | $CH_3$ | H | 92–93° C. |
| 14 | 4-$OC_2H_5$ | H | $CH_3$ | H | 1.5100 |
| 15 | 4-$OCH_2C\equiv CH$ | H | $CH_3$ | H | 1.5214 |

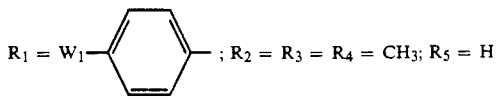

$R_1 = W_1-$ ; $R_2 = R_3 = R_4 = CH_3$; $R_5 = H$

| Example | $W_1$ | $R_6$ | $n_D^{20}$/m.p. |
|---|---|---|---|
| 16 | OH | $CH_3$ | 1.5259 |
| 17 | $OC_2H_5$ | $CH_3$ | 1.5138 |
| 18 | O—CH($CH_3$)$_2$ | H | 1.5486 |
| 19 | O—CH($CH_3$)$_2$ | $CH_3$ | 1.5854 |

-continued

| | | | |
|---|---|---|---|
| 20 | OCH$_2$–△–F,F (cyclopropyl with 2F) | H | 1.4998 |
| 21 | OCH$_2$CF$_3$ | H | 1.4779 |
| 22 | OCH$_2$CF$_3$ | CH$_3$ | 1.4776 |
| 23 | OCH$_2$–△–F,F | CH$_3$ | 1.5084 |
| 24 | OCH$_2$–△–Cl,Cl | CH$_3$ | 1.5294 |
| 25 | OCH$_2$–△–Cl,Cl | H | 1.5296 |
| 26 | OCH$_2$—CH=CH$_2$ | H | 1.5149 |
| 27 | OCH$_2$—CH=CH$_2$ | CH$_3$ | 1.5179 |
| 28 | 4-F-C$_6$H$_4$-O— | H | 1.5379 |
| 29 | 4-F-C$_6$H$_4$-O— | CH$_3$ | 1.5329 |
| 30 | OCHF$_2$ | H | 1.4877 |
| 31 | OCHF$_2$ | CH$_3$ | 1.4878 |
| 32 | OCH$_2$Ph | CH$_3$ | 85–88° C. |
| 33 | CH$_3$COO | H | 1.5586 |
| 34 | CH$_3$COO | CH$_3$ | 1.5087 |
| 35 | (CH$_3$)$_3$CCOO | H | 1.4878 |
| 36 | (CH$_3$)$_3$CCOO | CH$_3$ | 59–62° C. |
| 37 | PhCOO | H | 67–68° C. |
| 38 | PhCOO | CH$_3$ | 1.5432 |
| 39 | CH$_3$SO$_2$O | H | 95–98° C. |
| 40 | CH$_3$SO$_2$O | CH$_3$ | 1.5169 |
| 41 | CF$_3$SO$_2$O | H | 1.4687 |
| 42 | CF$_3$SO$_2$O | CH$_3$ | 1.4737 |

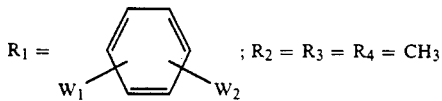

$R_1 =$ phenyl with W$_1$, W$_2$ substituents; $R_2 = R_3 = R_4 = CH_3$

| Example | W$_1$ | W$_2$ | R$_5$ | R$_6$ | $n_D^{20}$/m.p. |
|---|---|---|---|---|---|
| 43 | Cl | H | CH$_3$ | CH$_3$ | 1.513 |
| 44 | Cl | H | CH$_3$ | C$_2$H$_5$ | 1.510 |
| 45 | Cl | H | C$_2$H$_5$ | H | 1.509 |
| 46 | Cl | H | C$_2$H$_5$ | CH$_3$ | 1.512 |
| 47 | Cl | H | n-C$_3$H$_7$ | H | 1.504 |
| 48 | Cl | H | H | C$_2$H$_5$ | 1.516 |
| 49 | Cl | H | H | n-C$_3$H$_7$ | 1.513 |
| 50 | OCH$_2$CH$_2$Br | H | H | CH$_3$ | 1.503 |
| 51 | On-C$_3$H$_7$ | H | H | CH$_3$ | 1.503 |
| 52 | OCH$_3$ | 3-F | H | H | 1.505 |
| 53 | OCH$_3$ | 3-F | H | CH$_3$ | 1.508 |
| 54 | OC$_2$H$_5$ | 3-F | H | H | 1.501 |
| 55 | OC$_2$H$_5$ | 3-F | H | CH$_3$ | 1.503 |
| 56 | OCH$_2$CF$_3$ | 3-F | H | H | 1.468 |
| 57 | OCH$_2$CF$_3$ | 3-F | H | CH$_3$ | 1.475 |
| 58 | Cl | H | CH$_3$ | H | 1.510 |
| 59 | Cl | H | H | C(CH$_3$)$_3$ | 1.505 |
| 60 | OC$_2$H$_5$ | H | H | C(CH$_3$)$_3$ | 1.497 |
| 61 | OCH$_3$ | 3-F | H | C(CH$_3$)$_3$ | 1.495 |
| 62 | Cl | H | H | C(CH$_3$)$_2$OH | 1.510 |
| 63 | OC$_2$H$_5$ | H | H | CH$_2$Br | 1.509 |
| 64 | OC$_2$H$_5$ | H | CH$_3$ | H | 1.504 |
| 65 | OCH$_3$ | 3-F | CH$_3$ | H | 1.513 |
| 66 | OCH$_3$ | 3-F | H | C$_2$H$_5$ | 1.504 |
| 67 | OH | 3-Cl | H | H | 1.509 |
| 68 | OH | 3-Cl | H | CH$_3$ | 1.510 |
| 69 | OC$_2$H$_5$ | 3-Cl | H | H | 1.5215 |

-continued

| | | | | | |
|---|---|---|---|---|---|
| 70 | Cl | H | H | CH$_2$Cl | 1.5335 |
| 71 | OC$_2$H$_5$ | H | H | CF$_3$ | 1.4730 |
| 72 | OC$_2$H$_5$ | H | H | CH$_2$F | 1.5085 |
| 73 | CH$_3$ | H | H | CF$_3$ | 1.467 |
| 74 | OCH$_2$CH$_2$F | H | H | CH$_3$ | 1.511 |
| 75 | OC$_2$H$_5$ | H | —C≡CH | H | 1.5105 |
| 76 | OCH$_3$ | H | H | CH$_2$Cl | 1.5278 |
| 77 | OC$_2$H$_5$ | H | H | CH$_2$Cl | 1.5240 |
| 78 | OCH$_3$ | 3-Cl | H | H | 73-74.5° C. |
| 79 | OCH$_3$ | 3-Cl | H | CH$_3$ | 1.5290 |
| 80 | OC$_2$H$_5$ | 3-Cl | H | CH$_3$ | 1.5240 |
| 81 | OCH$_3$ | 3-Cl | H | CH$_2$Cl | 1.5380 |
| 82 | Cl | H | H | CH$_2$F | 1.516 |
| 83 | CH$_3$ | H | H | CH$_2$F | 1.505 |
| 84 | OC$_2$H$_5$ | 3-F | H | CF$_3$ | 29° C. |
| 85 | OCH$_3$ | 3-F | H | CH$_2$Cl | 1.5195 |
| 86 | OC$_2$H$_5$ | 3-F | H | CH$_2$Cl | 1.517 |
| 87 | OC$_2$H$_5$ | 3-F | CH$_3$ | H | 1.493 |
| 88 | OC$_2$H$_5$ | H | H | CH$_2$OCH$_3$ | 1.508 |
| 89 | C$_2$H$_5$ | H | H | CH$_3$ | 1.508 |
| 90 | C$_2$H$_5$ | H | H | H | 1.505 |
| 91 | C$_2$H$_5$ | H | CH$_3$ | H | 1.4982 |
| 92 | OC$_2$H$_5$ | 3-F | H | CH$_2$OH | 1.5121 |
| 93 | OC$_2$H$_5$ | H | H | CH$_2$OH | 1.524 |
| 94 | OCH$_2$CH$_2$F | H | H | H | 1.510 |
| 95 | Cl | H | —C≡CH | H | 1.5225 |
| 96 | OCH$_3$ | 3-F | —C≡CH | H | 1.512 |
| 97 | OC$_2$H$_5$ | 3-F | —C≡CH | H | 1.50 |
| 98 | C$_2$H$_5$ | H | —C≡CH | H | 1.5115 |
| 99 | C$_2$H$_5$ | H | H | CH$_2$OH | 1.5186 |
| 100 | C$_2$H$_5$ | H | H | CH$_2$F | 1.519 |
| 101 | OCHF$_2$ | 3-Cl | H | CH$_3$ | 1.493 |
| 102 | OCH$_2$CH$_2$F | 3-Cl | H | H | 1.516 |
| 103 | OSO$_2$CF$_3$ | 3-Cl | H | H | 1.5168 |
| 104 | OCHF$_2$ | 3-Cl | H | H | 1.4961 |
| 105 | OCH$_2$CH$_2$F | 3-Cl | H | CH$_3$ | viscous oil |
| 106 | OCH$_2$CF$_3$ | 3-Cl | H | H | viscous oil |
| 107 | OCH$_2$CF$_3$ | 3-Cl | H | CH$_3$ | viscous oil |
| 108 | OSO$_2$CF$_3$ | 3-Cl | H | CH$_3$ | viscous oil |
| 109 | n-C$_3$H$_7$ | H | H | H | viscous oil |
| 110 | n-C$_3$H$_7$ | H | H | CH$_3$ | viscous oil |
| 111 | n-C$_3$H$_7$ | H | CH$_3$ | H | viscous oil |
| 112 | OCHF$_2$ | 3-F | H | H | 1.4760 |
| 113 | OCHF$_2$ | 3-F | H | CH$_3$ | 1.4828 |
| 114 | OC$_2$H$_5$ | 3-F | H | CH$_2$F | 1.4995 |
| 115 | OCH$_2$CH$_2$F | 3-F | H | H | 1.4992 |
| 116 | OCH$_2$CH$_2$F | 3-F | H | CH$_3$ | 1.5003 |
| 117 | OSO$_2$CF$_3$ | 3-F | H | CH$_3$ | 1.4707 |
| 118 | OSO$_2$CF$_3$ | 3-F | H | H | 1.4646 |
| 119 | OC$_2$H$_5$ | H | H | CH$_2$OCCH$_3$ ‖ O | 1.6108 |
| 120 | CF$_3$O | H | H | CH$_3$ | 1.4680 |
| 121 | CF$_3$O | H | H | H | 1.4618 |
| 122 | CF$_3$O | H | CH$_3$ | H | 1,4614 |
| 123 | CF$_3$O | H | C≡CH | H | 1.4710 |
| 124 | CF$_3$ | H | H | H | 1.4690 |
| 125 | CF$_3$ | H | H | CH$_3$ | 1.4723 |
| 126 | CF$_3$ | H | CH$_3$ | H | 1.4646 |
| 127 | CF$_3$ | H | C≡CH | H | 1.4750 |
| 128 | CF$_3$ | H | C≡CHCH$_3$ | CH$_3$ | 62-3 |

The following test Examples demonstrate the biological activity of the compounds of the invention.

In all tests, the compounds were present in their racemic form.

TEST EXAMPLE A

Activity against larvae of the diamond-backed moth (*Plutella xylostella*).

The compounds of the invention were made up as aqueous emulsions at a concentration of 0.016%. Cabbage leaves (*Brassica olearacea var. botrytis*), placed in polystyrene petri dishes, were sprayed with these preparations (4 mg spray/cm$^2$). After the sprayed surface had dried, 10 young larvae of the diamond-backed moth (*Plutella xylostella*) were placed in each petri dish and thereby exposed to the treated food in the closed dishes for two days. The % mortality of the larvae after two days indicated the level of activity.

It was shown that the compounds of Examples 1, 2, 4, 5, 7, 8, 9, 11, 12, 14, 15, 31, 41, 42, 43, 45, 47, 48, 49, 52, 53, 54, 55, 56, 57, 58, 60, 64, 65, 66, 69, 70, 72, 74, 75, 78, 79 and 80 had 100% activity.

TEST EXAMPLE B

Activity against larvae (L2) of the cotton army worm (*Spodoptera littoralis*)

Compounds of the invention were made up as aqueous emulsions at a concentration of 0.04%. Leaflet pairs of beans (*Vicia fabae*) as well as 10 larvae (L2) of the cotton army worm (*Spodoptera littoralis*) per experiment were sprayed with 4 mg spray/cm$^2$ of these preparations in polystyrene petri dishes. The closed petri dishes were left in the laboratory under extended daylight conditions for two days. The % mortality of the larvae after two days indicated the level of activity.

It was shown that the compounds of Examples 1, 2, 11, 12, 18, 19, 21, 22, 30, 31, 41, 42, 43, 45, 47, 48, 49, 51, 52–58, 64, 65, 69, 72, 75, 77, 78 and 80 had 100% activity.

TEST EXAMPLE C

Ovicidal activity against eggs of the cotton army worm (*Spodoptera littoralis*).

The compounds of the invention were made up as aqueous emulsions at a concentration of 0.04%. One day old eggs that had been laid on filter paper by fertilised female moths were dipped in the preparations until they were completely wet and then placed in closed petri dishes in the laboratory under extended daylight conditions for four days. The % inhibition of hatching of the eggs in comparison with untreated eggs indicates the level of activity.

The compounds of Examples 1, 2, 12, 29, 43, 49, 52–58, 64, 65, 69–72, 77 and 78 had 100% activity.

TEST EXAMPLE D

Activity against larvae (L3) of the Mexican bean beetle (*Epilachna varivestis*)

The compounds of the invention were made up as aqueous emulsions at a concentration of 0.016%. French bean plants (*Phaseolus vulgaris*) in the primary leaf stage were dipped in the preparations. For each test two plant stems with in total four primary leaves were placed in glass vases filled with water and enclosed in plexiglass cylinders. Then five larvae of the Mexican bean beetle (*Epilachna varivestis*) at the third larval stage were put in the glass cylinders and kept for three days under extended daylight conditions. The % mortality of the larvae after three days indicated the level of activity.

With the compounds of Examples 1, 2, 8, 12 and 14, >90% activity was achieved.

TEST EXAMPLE E

Activity in prophylactic treatment of leaves against brown rice-hoppers (*Nilaparvata lugens Stal*)

In a heated greenhouse, rice seedlings (about 15 per pot) were grown until formation of the third leaf and then sprayed until dripping wet with an aqueous preparation containing 0.1% of active material. After drying the sprayed leaves, a transparent cylinder was placed over each pot. 30 Adult brown rice-hoppers (*Nilaparvata lugens*) were introduced into each pot. After 2 days at 26° C. in the greenhouse, the amount of dead hoppers was determined. The activity was calculated according to Abbott in comparison with several untreated control pots.

Complete death was reached with the compounds of Examples 1, 2, 4–15, 17–23, 26–33, 41, 42, 43–61, 64–66, 69, 70, 72, 74–81 and 120–128.

TEST EXAMPLE F

Activity in the curative treatment of broad beans (*Vicia fabae*) against black bean aphids (*Aphis fabae scop.*)

In a heated greenhouse, seedlings of broad beans (*Vicia fabae*)(one plant per pot) were grown to a height of about 6 cm. The plants were then covered with a culture of black bean aphid (*Aphis fabae*). After the each plant had been colonised with 100 to 200 insects, they were each sprayed with 0.1% of the respective active ingredient in an aqueous preparation until dripping wet and left in the glasshouse at about 24° C. After 2 days the amount of dead aphids was ascertained. The activity was calculated according to Abbott by comparison with untreated controls indicated the level of activity.

With the compounds of Examples 1, 2, 5, 8, 12, 14, 15, 17–19, 21–27, 31, 42, 43, 47, 48, 49, 51–57, 59–61, 64, 66, 69, 72, 74 and 80, 80 to 100% activity was achieved.

TEST EXAMPLE G

Insecticidal activity against *Musca domestica*

Aliquots of acetone solutions of test compounds at various concentrations were applied to 9 cm diameter filter papers placed in the bottom of 9 cm diameter petri dishes closed by glass lids. After evaporation of solvent, the treated surfaces, together with control treated with acetone alone, were then infested with adult houseflies, (*Musca domestica*) and held at 22° C. for 24 hours. The percentage mortality of the insects was then recorded.

Less than 5% mortality resulted in the control treatments whereas the compounds of Examples 1–7, 9–12, 14, 15, 17–19, 21, 22, 26, 27, 30, 31, 41, 42, 49, 51–53, 56, 58, 69, 72, 121 and 124–8 had an LC$_{50}$ of 300 mg/m$^2$ or less.

TEST EXAMPLE H

Insecticidal activity against *Lucilia sericata*

1 ml aliquots of an acetone solution containing test compound at various concentrations were applied to cotton wool dental rolls 1 cm×2 cm, contained in (2 cm diameter×5 cm long). After drying, the treated materials were then impregnated with 1 ml of nutrient solution, infested with first instar larvae of sheep blowfly (*Lucilia sericata*), closed by a cotton wool plug and held at 25° C. for 24 hours.

For the controls the mortality was <5% whereas the compounds of Examples 1–7, 9–12, 14–31, 39–42, 49–53, 56, 58, 69, 70, 72, 74, 76–81, 121 and 124–8 had an LC$_{50}$ of 300 ppm or less.

TEST EXAMPLE I

Tickicidal activity against *Boophilus microplus*

9 cm diameter filter papers were impregnated with 1 ml aliquots of acetone solutions of test compound at various concentrations. The papers were allowed to dry and then folded into envelopes in which cattle tick larvae, (*Boophilus microplus*) were enclosed and held at 25° C. and 80% R.H. for 48 hours. The percentage mortality of tick larvae was then recorded and compared with controls.

The controls gave a mortality of less than 5% whereas compounds of Examples 1, 2, 7, 9–15, 17, 21, 22, 26–31, 36, 39, 41, 42, 51–53, 56, 58, 69, 70, 124, 125 and 127 caused 50% mortality at a concentration of 300 ppm or less.

TEST EXAMPLE J

Insecticidal activity against *Blattella germanica*

Aliquots of acetone solutions of test compounds at various concentrations were applied to glass plates (10 cm×10 cm). After evaporation of solvent, the surfaces, together with controls treated with acetone alone, were then infested with second instar nymphs of the German cockroach, (*Blattella germanica*), retained on the treated surface within PTFE-coated glass rings 6 cm in diameter and held for 24 hours at 22° C. The percentage mortality of the insects wa then recorded.

Less than 5% mortality resulted in the control treatments whereas the compounds of Examples 2-7, 10-12, 14, 15, 17-19, 21-23, 26-34, 36, 40-42, 51-53, 56, and 58 had an $LD_{50}$ of 300 mg/m$^2$ or less.

TEST EXAMPLE K

Control of root knot nematode, *Meloidogyne incognita* (Chitwood 1949).

10% of a powder preparation of the active ingredient prepared according to preparation No. I was mixed thoroughly with soil that had been strongly infested with the test nematode. After this the treated soil was put into a 0.5 liter fermenting tube, treated with cucumber seeds and cultivated at a soil temperature of 25° to 27° C. in a greenhouse. After a cultivation time of 25to 28 days the cucumber roots were washed and inspected in a water bath for nematode attack (root knots) and the % level of activity of the active ingredients compared with a treated control was determined. When the nematode attack is fully controlled the level of activity is 100%.

At a dose of 200 mg or less of active substance per liter of soil, a nematode attack by Meloidogyne incognita was at least 90% controlled by compounds of Examples 1, 2, 11, 12, 14, 17-19, 21, 22, 27, 30, 31, 50-59, 65 and 69-71.

TEST EXAMPLE L

Soil insecticide activity against eggs/larvae of the corn rootworm (*Diabrotica undecimpunctata*)

Formulations of test compounds were made up as aqueous suspensions at various concentrations. 5 ml of these suspensions were pipetted onto 50 ml soil in a 250 ml plastic pot. About 50 eggs of the corn rootworm (*Diabrotica undecimpunctata*) as well as 2 sprouting maize (*Zea mays*) seeds were placed in each pot. The pots were left in the glasshouse under extended daylight conditions and at 24°-26° C. for 14 days. The mortality of the *Diabrotica* was assessed after 10 days in comparison with untreated controls.

At a dose of 64 ppm of active substance a mortality of 80-100% was achieved by the compounds of Examples 1, 2, 11-14, 17-19, 21, 22, 27, 30, 31, 42, 43, 45, 47-59, 61, 64, 65, 69-72, 77, 80, 87-89, 94-98, 100-107, 110-117, 120-123 and 125-128.

COMPARISON EXAMPLE

Various compounds of the invention were directly compared with their isopropyl analogues ($R_4$=H) in UK Patent No 2161163 (equivalent to U.S. Pat. No. 4668815—Enari et al), using the previously described test in Test Example L for soil insecticide activity against eggs and larvae of the corn rootworm (*Diabrotica undecimpunctata*):

In all tests, the compounds were present in their racemic form.

The results are as follows:

| Compound | Rate (ppm) | Compound of Invention ($R_4$ = Me) | | Compound of UK 2161163 ($R_4$ = H) | |
|---|---|---|---|---|---|
| | | Ex No | mortality (%) | Cpd No | mortality (%) |
| $R_1$ = 4-Cl—Ph | | 1 | | 14 | |
| $R_5$ = H | 25 | | 100 | | 0 |
| $R_6$ = Me | 10 | | 90 | | 0 |
| $R_1$ = 4-EtO—Ph | | 14 | | 1 | |
| $R_5$ = H | 1.6 | | 100 | | 50 |
| $R_6$ = H | | | | | |
| $R_1$ = 4-EtO—Ph | | 17 | | 2 | |
| $R_5$ = H | 1.6 | | 100 | | 50 |
| $R_6$ = Me | | | | | |
| $R_1$ = 4-EtO,3F—Ph | | 54 | | 33 | |
| $R_5$ = H | 25 | | 90 | | 0 |
| $R_6$ = H | 10 | | 90 | | 0 |
| $R_1$ = 4-EtO—Ph | | 64 | | 12 | |
| $R_5$ = Me | 25 | | 100 | | 0 |
| $R_6$ = H | 10 | | 0 | | 0 |

WE CLAIM
1. Phenylacetic acid derivatives of general formula I

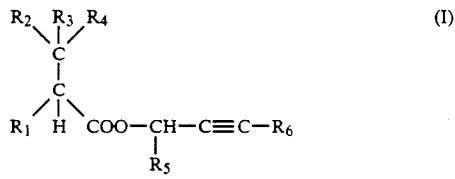

in which
$R_1$ is phenyl, optionally substituted by one or more of the same or different groups selected from halogen, hydroxy, $C_{1-4}$-alkyl, halo-$C_{1-4}$-alkyl, $C_{3-6}$-cycloalkyl, halo-$C_{3-6}$-cycloalkyl, $C_{1-6}$-alkoxy, (optionally substituted by halogen, $C_{1-4}$-alkoxy, $C_{1-4}$-alkylthio, $C_{1-4}$-aklylamino or di-$C_{1-4}$-alkylamino), $C_{2-6}$-alkynyloxy, halo-$C_{2-6}$-alkynyloxy, $C_{2-6}$-alkenyloxy, halo-$C_{2-6}$-alkenyloxy, $C_{3-6}$-cycloalkoxy, (optionally substituted by halogen , $C_{3-6}$-cycloalkylmethoxy, halo-$C_{3-6}$-cycloalkylmethoxy, $C_{1-6}$-alkylthio, (optionally substituted by halogen), $C_{1-6}$-alkylsulphinyl, $C_{1-6}$-alkylsulphony, phenoxy, halophenoxy, amino, $C_{1-4}$-alkylamino, di-$C_{1-4}$-alkylamino, cyano, nitro and the group OX, wherein X is the acyl group $R_7CO$ or the sulphonyl group $R_7SO_2$, in which $R_7$ is $C_{1-6}$-alkyl, (optionally substituted by halogen, $C_{1-4}$-alkoxy, $C_{1-4}$-alkylamino or di-$C_{1-4}$-alkylamino), $C_{3-6}$-cycloalkyl, (optionally substituted by halogen), $C_{2-6}$-alkynyl, (optionally substituted by halogen), $C_{2-6}$-alkenyl or phenyl;

$R_2$, $R_3$ and $R_4$ are the same or different and are $C_{1-4}$-alkyl, optionally substituted by halogen, $C_{2-6}$-alkoxy and/or $C_{1-4}$-alkylthio;

$R_5$ and $R_6$ are the same or different and are hydrogen, $C_{1-4}$-alkyl or $C_{3-6}$-cycloalkyl, each optionally substituted by halogen, $C_{1-4}$-alkoxy, $C_{1-4}$-alkylthio, $C_{1-4}$-alkylamino or di-$C_{1-4}$-alkylamino; $C_{2-6}$-alkenyl or $C_{2-6}$-alkynyl, each optionally substituted by halogen, or $C_{1-6}$-alkyl, substituted by the group —OY, wherein Y is hydrogen, the acyl group $R_7CO$ or the sulphonyl group $R_7SO_2$, in which $R_7$ has the meaning given above.

2. Compounds according to claim 1, in which $R_1$ is phenyl, substituted in the para position by $C_{1-3}$-methyl, halogen, trifluoromethyl, $C_{1-2}$-alkoxy or $C_{1-2}$-fluoroalkoxy, and optionally substituted in the meta position by fluorine or chlorine;

$R_2$, $R_3$ and $R_4$ are methyl;

$R_5$ is hydrogen or acetylenyl; and $R_6$ is hydrogen or methyl.

3. Compound according to claim 2 in which $R_1$ is p-trifluoromethylphenyl, $R_5$ is acetylenyl and $R_6$ is hydrogen.

4. Compound according to claim 2 in which $R_1$ is p-ethoxyphenyl, $R_5$ is methyl and $R_6$ is hydrogen.

5. An insecticidal and acaricidal composition which comprises a compound claimed in claim 2, in admixture with an agriculturally acceptable diluent or carrier.

6. An insecticidal and acaricidal composition which comprises a compound claimed in claim 3, in admixture with an agriculturally acceptable diluent or carrier.

7. An insecticidal and acaricidal composition which comprises a compound claimed in claim 4, in admixture with an agriculturally acceptable diluent or carrier.

8. A method of combating insects and acarids which comprises applying to the insects or acarids or their locus an effective amount of a compound claimed in claim 1.

9. A method of combating insects and acarids which comprises applying to the insects or acarids or their locus an effective amount of a compound claimed in claim 2.

10. A method of combating insects and acarids which comprises applying to the insects or acarids or their locus an effective amount of a compound claimed in claim 3.

11. A method of combating insects and acarids which comprises applying to the insects or acarids or their locus an effective amount of a compound claimed in claim 4.

* * * * *